United States Patent [19]

Cavani et al.

[11] Patent Number: 5,650,547
[45] Date of Patent: Jul. 22, 1997

[54] CATALYST FOR THE ALKYLATION OF AROMATIC COMPOUNDS AND PROCESS WHICH MAKES USE OF SAID CATALYST

[75] Inventors: Fabrizio Cavani; Gianni Girotti, both of Bologna; Virginio Arrigoni, Milan; Giuseppe Terzoni, Piacenza, all of Italy

[73] Assignee: Ministero Dell 'Universita' E Della Ricerca Scientifica E Technologica, Italy

[21] Appl. No.: 466,233

[22] Filed: Jun. 6, 1995

Related U.S. Application Data

[63] Continuation of Ser. No. 145,038, Oct. 28, 1993, abandoned, which is a continuation of Ser. No. 29,114, Mar. 10, 1993, abandoned, which is a division of Ser. No. 903,602, Jun. 24, 1992, abandoned.

[30] Foreign Application Priority Data

Jul. 1, 1991 [IT] Italy .................................. 001811A/91

[51] Int. Cl.$^6$ .................................. C07C 2/66; C07C 4/00
[52] U.S. Cl. .................................. 585/467; 585/446; 585/466; 585/475
[58] Field of Search .................................. 585/446, 466, 585/467, 475

[56] References Cited

U.S. PATENT DOCUMENTS

| | | | |
|---|---|---|---|
| 3,251,897 | 5/1966 | Wise | 260/671 |
| 3,631,120 | 12/1971 | Eberly, Jr. et al. | 260/671 |
| 3,755,483 | 8/1973 | Burress | 260/671 R |
| 4,044,065 | 8/1977 | Butter et al. | 260/677 R |
| 4,115,424 | 9/1978 | Unland et al. | 252/432 |
| 4,128,592 | 12/1978 | Kaeding | 260/671 C |
| 4,291,185 | 9/1981 | Kaeding | 585/467 |
| 4,379,761 | 4/1983 | Olson et al. | 252/435 |
| 4,393,262 | 7/1983 | Kaeding | 585/467 |
| 4,421,941 | 12/1983 | Olson et al. | 585/467 |
| 4,429,174 | 1/1984 | Teng et al. | 585/426 |
| 4,459,426 | 7/1984 | Inwood et al. | 585/323 |
| 4,483,936 | 11/1984 | Liu et al. | 502/74 |
| 4,727,209 | 2/1988 | Chao | 585/466 |
| 4,798,816 | 1/1989 | Ratcliffe et al. | 502/62 |
| 4,839,319 | 6/1989 | Schuette et al. | 502/64 |
| 4,970,183 | 11/1990 | Nakamoto et al. | 502/68 |

FOREIGN PATENT DOCUMENTS

| | | |
|---|---|---|
| 0252761 | 1/1988 | European Pat. Off. . |
| 0397183 | 11/1990 | European Pat. Off. . |
| 2212219 | 9/1987 | Japan . |
| 0479485 | 8/1975 | U.S.S.R. . |
| 9014160 | 11/1990 | WIPO . |

OTHER PUBLICATIONS

Journal of Catalysis, Organic Reactions Catalyzed By Crystalline Aluminosilicates, vol. 5, Venuto et al., pp. 484–493 (1966).

Journal of Catalysis, Shape–Selective Reactions With Zeolite Catalysts, Kaeding et al., vol. 89, pp. 267–273 (1984).

*Primary Examiner*—Ponnathapura Achutamurthy
*Attorney, Agent, or Firm*—George P. Hoare, Jr.; Rogers & Wells

[57] ABSTRACT

This invention provides a process for the selective production of cumene comprising reacting benzene with propylene in the presence of a type-Y zeolite modified by treatment with a phosphorous compound. This invention also provides a process for the transalkylation of a polyalkylated benzene which comprises reacting the polyalkylated benzene in the presence of benzene and a type-Y zeolite modified by treatment with a phosphorous compound.

16 Claims, No Drawings

CATALYST FOR THE ALKYLATION OF AROMATIC COMPOUNDS AND PROCESS WHICH MAKES USE OF SAID CATALYST

This is a continuation divisional, of application Ser. No. 07/903,602 filed Jun. 24,1992 abandoned.

The present invention relates to an improved procedure for the alkylation of aromatic compounds with $C_2$–$C_5$ olefins, a procedure which uses a catalyst obtained by impregnating a zeolite Y with a solution of a phosphorous compound; the invention also relates to this catalyst and the method for its preparation.

More specifically, the present invention relates to the preparation of a catalyst by impregnating a zeolite Y with phosphorous compounds and the use of the catalyst thus obtained in the alkylation reaction of benzene with propylene to form cumene.

At present most processes for the production of cumene use a catalytic system composed of phosphoric acid on infusorial earth or kieselgumr catalysts of the same type—suitably modified—are used in the production of oligomers of propylene.

The main advantages of this catalytic system lie in the low production costs and high selectivity towards cumene; on the other hand the acidity and impossibility of regeneration cause problems of corrosion in the plants and—above all—for disposal of the exhausted catalyst.

Another catalytic system composed of aluminium trichloride and hydrochloric acid in slurry is at present used on an industrial scale, but also this has problems relating to the high corrosivity of the system and difficulties in separating this from the reaction mixture.

To overcome the above draw-backs different kinds of processes have been proposed, using as a heterogeneous catalyst, a zeolite, possibly modified following suitable treatment and/or by the addition of rare earth.

U.S. Pat. Nos. 4,393,262, 3,755,483 and 4,291,185 describe the use of a zeolite of the HZSM 12 type in the synthesis of cumene.

U.S. Pat. No. 3,251,897 describes the alkylation of aromatic hydrocarbons in the presence of zeolites of the Y and X types and specifically of zeolites wherein the cations are rare earth and/or hydrogen.

U.S. Pat. No. 3,631,120 describes an alkylation process of benzene with zeolites with a ratio Si/Al of 4.0 to 4.9 in acid form.

These systems are characterized by their regenerability by means of thermal treatment, by operating in a heterogeneous phase and by being easily processed and transportable.

Among all known systems for the alkylation reaction of benzene to cumene, which generally differ by their different activities and selectivity, the most promising from an industrial point of view is undoubtedly the system based on the type-Y zeolite.

This catalytic system is characterized by a good activity—it can in fact operate at temperatures ranging from 150° to 180° C.—and good selectivity towards cumene.

The possibility of operating at low temperatures is a very important factor for this type of reaction, because, in these catalysts, one of the causes of disactivation is the polymerization of the olefin and subsequent cyclization forming aromatics with large dimensions which cannot migrate out of the microporous structure present in the zeolite crystal (Venuto et Al., J. Catalysis 5, 384–493, 1966; IEC 190–192, September 1967). In addition there is also the effect of the formation of carbon due to dehydrogenating cracking reactions also favoured at higher temperatures.

With respect to the type-Y zeolite, this, however, is characterized by a sensitive reduction in the selectivity along with the increasing in the conversion of the benzene.

The advantage of a selectivity which remains high, even at high conversions of benzene, lies in the possiblity of operating even with low feeding molar ratios Benzene/Olefin and consequently reducing some of the costs related to recycling the converted benzene.

Zeolite Y, on the other hand, is able to convert polyalkylated products into cumene owing to its acid properties which cause the transalkylation reaction; to do this it is preferable to use a second reactor where a mixture of polyalkylates (mainly diisopropylbenzene, in the synthesis of cumene) and benzene are fed under specific conditions. This naturally leads to higher investment and plant management costs connected not only to the cost of the second reactor but also to the necessary separation of the polyalkylates from the heavier products.

It is not possible to recycle the polyalkyates in the same reactor where the alkylation is carried out because the transalkylation reaction generally takes place under different conditions than those present in the primary reactor (higher temperatures).

Attempts have been made to improve the performance of zeolite Y by an exchange with rare earth (U.S. Pat. No. 3,251,897) or by means of deposition treatment of carbon which produces a 1% increase in the selectivity to cumene (U.S. Pat. No. 4,798,816). These, however, have not succeeded in completely eliminating the above draw-backs.

It is known that zeolites of the ZSM 5 type can be treated with phosphorous compounds (U.S. Pat. No. 4,128,592) to obtain modified catalytic forms with an improved selectivity; e.g. in alkylation reactions of toluene with ethylene, this improvement can be seen by a high increase of the selectivity to the para-position (Journal of Catalysis 89, 267–273, 1984).

The Applicant has now found that by treating type-Y zeolites with phosphorous compounds, catalytic forms are obtained which produce a considerable improvement in the selectivity in the formation of desired alkylated products starting from aromatic substrates (particularly in the preparation of cumene starting from benzene), and that this selectivity is barely or not at all influenced by an increase in the conversion of the aromatic substrate. Moreover the use of these catalytic forms leads to a reduced formation of polyalkylated products with a consequent decrease in the relative costs of their treatment, as previously specified.

The present invention consequently relates to an improved process for the alkylation, with $C_2$–$C_5$ olefins, of aromatic compounds, carried out in the presence of a catalyst composed of a type-Y zeolite modified by treatment with a phosphorous compound.

The invention also relates to the catalyst thus obtained, as well as to the method for its preparation including impregnation of the particular zeolite with a solution, which may or may not be aqueous, of a phosphorous compound and subsequent drying/calcination of the material thus obtained.

The final catalyst obtained is particularly active in alkylation reactions of benzene with $C_2$–$C_5$ olefins and, particularly, in the alkylation of benzene with propylene.

Y zeolites suitable for the purpose are normally available on the market or synthesized using the known methods.

Before treatment the zeolite, which may or may not be in acid form, can be calcinated in the presence of water vapour for a period of 1 to 24 hours at a temperature ranging from 400° to 700° C.

The impregnation treatment is carried out by putting the zeolite in contact with solutions, which may or may not be aqueous, containing phosphorous compounds and subjecting the material thus obtained to conventional drying and/or calcination.

The final quantity of phosphorous present on the catalyst will range from 0.1% to 25% by weight, and preferably from 0.1% to 8% by weight of phosphorous.

Different phosphorous compounds may be used for the impregnation treatment.

Suitable compounds may therefore be represented by derivatives containing one or more of the following groups: $PX_3$, $RPX_2$, $R_2PX$, $R_3P$, $X_3PO$, $(XO)_3PO$, $(XO)_3P$, $R_3P=O$, $R_3P=S$, $RPO_2$, $PPS_2$, $RP(O)(OX)_2$, $RP(SX)_2$, $ROP(OX)_2$, $RSP(SX)_2$, $(RS)_2PSP(SR_2)$, $(RO)_2POP(OR)_2$, $(RO)_2POP(OR)_2$ wherein R is $C_1-C_{10}$ alkyl or $C_6-C_{30}$ aryl, and X is hydrogen, ammonium R or a halogen such as chlorine, bromine, fluorine and iodine.

These compounds also include $RPH_2$ primary phosphines, $R_2PH$ secondary, and $R_3P$ tertiary phosphines; $R_3PS$ tertiary phosphinic sulphides; $RP(O)(OX)_2$ primary and $R_2P(O)OX$ secondary phosphinic acids; the corresponding sulphurate derivatives such as $RP(S)(SX)_2$ and $R_2P(S)SX$; the esters of phosphonic acids such as $(RO)_2P(O)H$, $(RO)_2P(O)R$, $(RO)P(O)R_2$; $R_2POX$ phosphinous acids; their phosphite and ester derivatives. The corresponding derivatives containing sulphur may also be used, such as, for example, $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RA)$ $(PR_2)$ and $(RS)_2PR$.

Among the above compounds those of phosphoric acid, polyphosphoric acid, mixtures of polyphosphoric acids, acid and non-acid ammonium phosphates, primary, secondary and tertiary phosphines, are particulary preferred.

The treatment which produces the modified zeolite, i.e. impregnation and reaction of the Y zeolite with the solution of the phosphorous compound, can be carried out on the zeolite in powder form, whether in acid form or in the form of ammonium salt.

When the treatment is carried out on zeolite in powder, before being used in the reaction, the treated zeolite should be mixed with suitable binders; for this purpose silicon, aluminium, zirconium, magnesium oxides or natural clay oxides can be used or combinations of the above.

After mixing, a paste is obtained which is fed to an extruder or other machines for the desired moulding.

The products of the moulding operations are then calcined at a temperature ranging from 300° to 700° C.

If the treatment is carried out on zeolitic catalysts which have already been formed, the treated zeolite is subjected to thermal treatment at temperatures ranging from 150° to 700° C; preferably from 400° to 700° C.

The alkylation reaction may be carried out in continuous, semi-continuous or batch-wise, but preferably in continuous.

The reaction is carried out at a temperature ranging from 100° to 300° C., preferably from 110° to 200° C., at a pressure of 10 to 50 atms, preferably from 30 to 40 atms and with a feeding rate aromatic+olefin of 0.2 to 200 $h^{-1}$ but preferably from 0.5 to 10 $h^{-1}$; the alkylation reaction is preferably carried out in a flow reactor.

The reaction may be carried out in a gaseous phase, liquid phase and mixed phase; it is preferably however to operate in a liquid phase, in that this makes it possible to minimize the formation of tars and carbon by-products and lengthen the catalyst life by the washing action which the presence of the liquid phase guarantees with respect to a gaseous phase.

The feeding molar ratio between aromatic compound and olefin can vary from 2/1 to 30/1, it is preferable to operate within a range of 4/1 to 10/1.

Within this range of molar ratios the polyalkylation reaction and polymerization of the olefin are minimized allowing a greater duration period between two subsequent regenerations of the catalyst.

The above catalyst is also active in transalkylation processes of polyalkylates carried out in the presence of benzene and above all in the transalkylation of diisopropylbenzene (DIPB) which are by-products of the alkylation of benzene with propylene.

The feeding molar ratio between benzene and DIPB can vary from 5/1 to 40/1 and the temperature of the transalkylation reaction can range from 150° C. to 250° C., at a pressure of 1 to 40 atms and with a feeding rate of the reagents of 0.5 to 30 $h^{-1}$.

The reaction is preferably carried out in the liquid phase.

The regeneration of the catalyst can be carried out by thermal treatment with gases containing oxygen (such as air) with a suitable temperature profile and maximum temperature of 500° to 700° C. to burn the carbon residues deposited inside the zeolitic structure of the catalyst, without damaging the structure itself.

EXAMPLE 1

Y zeolite extrudates are used in acid form and having the following characteristics:

$SiO_2/Al_2O_3$: 5.9 Molar (in the zeolitic structure)

BINDER: clay; content: 25% of the zeolite powder

PELLET DIAMETER: 1.5 mm 10 g of the above zeolite are put in contact with 50 ml of an aqueous solution containing 0.37 g of $H_3PO_4$ (0.1 g as P).

The system is left to rest for 5 hours with occasional stirring and the water is subsequently slowly evaporated to dryness.

The solid is thermally treated at 150° C. for 2 h and subsequently at 500° C. for a further 2 h.

The product obtained contains a phosphorous percentage, equal to 1% by weight (calculated as P).

X-ray analysis showed that the zeolite structure have not been modified.

4.65 g of the catalyst thus prepared are put in a cylindrical reactor having a length of 15 cm and diameter of 1.5 cm diluted with at least 1 volume of quartz chips having a low surface area.

A thermowell is placed along the main axis of the reactor with a thermocouple which slides along said axis to measure the temperature in the catalytic bed.

A mixture of benzene and propylene prepared by directly weighing the single compounds to obtain the required molar ratio benzene/propylene, is fed to the reactor.

The mixture is kept in a pressure tank at 20 atms and sent to the reactor by means of a volumetric pump.

The reactor is situated inside a thermostat-regulated chamber at the test temperature which shows a maximum ΔT of 0.1° C.; the maximum ΔT existing along the main axis of the reactor during each test is 1° C.

A valve is situated at the outlet of the reactor to keep the pressure at the indicated test value and is followed by a condenser where the reaction products are collected while the uncondensable products are measured with a volume meter and continuously analyzed.

In Table I below the tests at different benzene conversions obtained by variation of the contact time within the indicated range of WHSV.

As can be seen, the Table shows the conversion values of benzene and propylene and the selectivity to cumene (CUM), to diisopropylbenzenes (DIPB) with the distribution of isomers and to triisopropylbenzenes (TIPB).

When the catalyst used in the tests is discharged, after 120 hours of reaction, the percentage of phosphorous present is equal to 1%.

TABLE 1

EXAMPLE N. 1
MODIFIED ZEOLITE

| n | ConvC6 | ConvC3- | CUM | Tipb | Dipb | (m | o | p) |
|---|---|---|---|---|---|---|---|---|
| 1 | 7.6 | 66.6 | 89.1 | 0.11 | 10.6 | (61; | 2; | 37) |
| 2 | 8.3 | 72.9 | 89.2 | 0.11 | 10.7 | (61; | 3; | 36) |
| 3 | 9.1 | 79.1 | 89.3 | 0.11 | 10.4 | (62; | 2; | 36) |
| 4 | 9.5 | 83.0 | 88.7 | 0.10 | 11.1 | (61; | 3; | 36) |
| 5 | 9.7 | 85.4 | 88.5 | 0.11 | 11.2 | (62; | 3; | 35) |
| 6 | 10.5 | 92.4 | 88.4 | 0.12 | 11.3 | (62; | 3; | 35) |

R = [C6]/[C3-] = 7.6 P = 30 ats T = 150 C.
WHSV from 0.8 to 1.7

EXAMPLE 2

Zeolite Y without modification was used in the same experimental apparatus as Example 1 and exactly under the same conditions.

The aim is to compare the results with those obtained in Example 1, approximately within the same conversion range of benzene where the influence of the transalkylation reactions of benzene to the final selectivity value to cumene is reduced to the minimum.

The drop in selectivity to cumene between tests 1 and 4 in Table 2 is about double compared to the data shown in Table 1 and all the selectivity values to cumene can be found 1.5 points below the selectivity values shown in Table 1 in the same conversion range.

The TIPB and DIPB fractions are higher with respect to the values of Example 1 which confirms that in this reaction the selectivity to cumene is mainly influenced by these compounds.

TABLE 2

EXAMPLE N 2
ZEOLITE Y

| n | ConvC6 | ConvC3- | CUM | Tipb | Dipb | (m | o | p) |
|---|---|---|---|---|---|---|---|---|
| 1 | 7.9 | 69.3 | 88.1 | 0.26 | 11.3 | (61; | 3; | 36) |
| 2 | 9.3 | 82.1 | 87.0 | 0.26 | 12.4 | (61; | 3; | 36) |
| 3 | 10.0 | 89.4 | 86.2 | 0.26 | 13.3 | (61; | 2; | 36) |
| 4 | 10.5 | 92.5 | 86.0 | 0.26 | 13.3 | (61; | 2; | 37) |
| 5 | 10.8 | 96.8 | 85.6 | 0.27 | 13.9 | (61; | 2; | 37) |

R = [C6]/[C3-] = 7.6 P = 30 Ata T = 150 C.
WHSV from 0.8 to 1.7

EXAMPLE 3

The experimental apparatus and catalyst are the same as those used in Example 1 as are all the reaction conditions except for the temperature which was modified as shown in Table 3.

At a temperature of 170° C. the selectivity value to cumene was definitely influenced by the transalkylation reactions and in fact the values shown in Table 3, in the same conversion range of benzene, are higher than those of Examples 1 and 2.

The selectivity values to cumene are quite constant within the whole conversion range up to the maximum conversion value of propylene.

The distribution of the DIPB isomers is basically similar to that of Examples 1 and 2 and near the equilibrium value.

TABLE 3

EXAMPLE N. 3
MODIFIED ZEOLITE

| n | ConvC6 | ConvC3- | CUM | Tipb | Dipb | (m | o | p) |
|---|---|---|---|---|---|---|---|---|
| 1 | 7.6 | 63.8 | 95.0 | 0.035 | 4.7 | (63; | 3; | 3) |
| 2 | 9.2 | 76.4 | 93.1 | 0.028 | 6.9 | (61; | 3; | 36) |
| 3 | 9.5 | 79.2 | 93.5 | 0.026 | 6.0 | (60; | 4; | 36) |
| 4 | 9.8 | 81.8 | 93.9 | 0.025 | 5.8 | (62; | 3; | 35) |
| 5 | 10.2 | 85.2 | 93.5 | 0.029 | 6.0 | (61; | 4; | 35) |
| 6 | 10.5 | 87.5 | 93.7 | 0.037 | 5.8 | (62; | 4; | 34) |
| 7 | 10.9 | 88.5 | 93.3 | 0.031 | 6.2 | (61; | 4; | 35) |
| 8 | 11.6 | 96.4 | 93.0 | 0.038 | 6.5 | (60; | 5; | 35) |
| 9 | 11.9 | 99.8 | 93.1 | 0.044 | 6.5 | (61; | 4; | 35) |

R = [C6]/[C3-] = 7.6 P = 30 Ats T = 170 C.
WHSV from 0.8 to 1.7

EXAMPLE 4

The Y zeolite without modification was tested under the same conditions as used in Example 3 and the values found are shown in Table 4.

The selectivity to cumene is at least 1 point % lower than the data of Example 3 due, as can be seen, to the formation of 20% more of DIPB and a double quantity of TIPB.

Also in this series of tests at T=170° C. the distribution of DIPB isomers is more or less similar to the data of the previous examples and consequently the treatment carried out on the catalyst in Example 3 evidently does not induce p-selectivity in this reaction.

TABLE 4

EXAMPLE N. 4
ZEOLITE Y

| n | ConvC6 | ConvC3- | CUM | Tipb | Dipb | (m | o | p) |
|---|---|---|---|---|---|---|---|---|
| 1 | 10.0 | 84.1 | 92.8 | 0.074 | 6.7 | (62; | 3; | 35) |
| 2 | 10.3 | 86.1 | 92.5 | 0.082 | 7.1 | (61; | 3; | 36) |
| 3 | 10.6 | 87.7 | 92.1 | 0.077 | 7.4 | (61; | 3; | 36) |

R = [C6]/[C3-] = 7.6 P = 30 Ats T = 170 C.
WHSV from 0.8 to 1.7

EXAMPLE 5

10 g Of the zeolite having the characteristics of Example 1 are put in contact with 50 ml of an aqueous solution containing $NH_4H_2PO_4$ in quantities of 0.3 total grams expressed as phosphorous.

The system is then treated as described in Example 1.

The catalyst thus obtained contains 3% of P and on XRD analysis showed no modification in the zeolitic structure.

It gave a selectivity to cumene of 88.5% at a 9.6% conversion of benzene, under the same conditions as Example 1.

Under the same conditions as Example 3 the selectivity to cumene was 93.1% at an 11.9% conversion of benzene.

EXAMPLE 6

Using the same zeolite as Example 1 a preparation is carried out as described in Example 1 but after drying the system, the solid thus obtained is thermally treated at 200° C. for 2 h.

Analysis showed the same characteristics of the material obtained with the procedure indicated in Example 1.

The catalyst thus obtained was tested under the same conditions as Example 1 showing a selectivity to cumene of 88.5% at a 9.7% conversion of benzene.

The same material under the conditions of Example 3 gave a selectivity to cumene of 92.5% at an 11.5% conversion in benzene.

EXAMPLE 7

A Y zeolite is used in ammonium form in powder having the following characteristics:

$Si_2O_3/Al_2O_3=5.9$ 10 g of this zeolite are put in contact with 50 ml of an aqueous solution containing 0.74 g of 85% $H_3PO_4$ (0.2 g as P).

The system is kept under mechanical stirring at room temperature for 10 h.

The excess water is subsequently evaporated slowly.

The solid thus obtained is thermally treated at 150° C. for 2 h and subsequently at 550° C. for a further 4 h.

The product obtained contains 2% by weight of phosphorous.

X-ray analysis showed that the zeolitic structure had not undergone modification.

The material thus obtained is charged in an 0.5 l autoclave in a quantity of 2 g and with a quantity of benzene equal to 200 cc.

The quantity of propylene necessary to have the molar ratio indicated in Table 5 is subsequently charged.

The tests with different conversions of benzene are carried out keeping the system under reaction conditions for different times.

As can be seen from the results of tests 1, 2 and 3 even with very low molar ratios of benzene and propylene, the selectivity to cumene maintains good values.

In the group of tests with higher feeding ratios (C6/C3= 7.6) the effect of the transalkylation reaction on an increase in the conversion in benzene is evident; the data at higher conversion can be compared to the values obtained in Example 3.

TABLE 5

EXAMPLE N. 7
MODIFIED ZEOLITE

| n | [C6]/[C3-] | ConvC6 | ConvC3- | CUM | Dipb | Tipb |
|---|---|---|---|---|---|---|
| 1 | 2 | 21.8 | 49.8 | 88.2 | 10.4 | 0.10 |
| 2 | 3 | 8.7 | 30.5 | 89.4 | 9.7 | 0.06 |
| 3 | 3 | 16.1 | 57.5 | 84.9 | 13.3 | 0.12 |
| 4 | 7.6 | 7.2 | 62.3 | 89.9 | 9.3 | 0.02 |
| 5 | 7.6 | 9.7 | 84.3 | 89.0 | 9.7 | 0.03 |
| 6 | 7.6 | 10.3 | 86.0 | 92.8 | 6.6 | 0.01 |
| 7 | 7.6 | 10.8 | 90.4 | 93.9 | 5.5 | 0.01 |

Autoclave test P = 30 atms: T = 170° C.

We claim:

1. A process for preparing cumene comprising reacting benzene with propylene in the presence of a catalyst under suitable reaction conditions, wherein the catalyst consists of zeolite Y modified by treatment with a phosphorous compound.

2. Process according to claim 1 characterized in that the reaction is carried out at a temperature ranging from 100° to 300° C.

3. Process according to claim 2 characterized in that the reaction is carried out at a temperature ranging from 110° to 200° C.

4. Process according to claim 3, characterized in that the reaction is carried out at a pressure of 10 to 50 atms.

5. Process according to claim 4 characterized in that the reaction is carried out at a pressure of 30 to 40 atms.

6. Process according to claim 1, characterized in that the reaction is carried out at a combined WHSV (weight hourly space velocity) for benzene and propylene of 0.2 to 200 $h^{-1}$.

7. Process according to claim 6 characterized in that the reaction is carried out at a WHSV of 0.5 to 10 $h^{-1}$.

8. Process according to claim 1, characterized in that the feeding molar ratio between benzene and propylene varies from 2/1 to 30/1.

9. Process according to claim 8, characterized in that the feeding molar ratio between benzene and propylene ranges from 4/1 to 10/1.

10. Process, according to claims 1, characterized in that it is carried out in a flow reactor.

11. A process for the transalkylation of a polyalkylated benzene which comprises reacting the polyalkylated benzene in the presence of benzene and a catalyst under suitable reaction conditions, wherein the catalyst consists of zeolite Y modified by treatment with a phosphorous compound.

12. Process for the transalkylation of a polyalkylated benzene according to claim 11, wherein the reaction is carried out starting from diisopropylbenzene (DIPB).

13. Process for the transalkylation of a polyalkylated benzene according to claim 12, wherein the feeding molar ratio benzene/(DIPB) ranges from 5/1 to 40/1.

14. Process for the transalkylation of a polyalkylated benzene according to claim 11, wherein the reaction is carried out at a temperature ranging from 150° to 250° C.

15. Process for the transalkylation of a polyalkylated benzene according to claim 11, wherein the reaction is carried out at a pressure ranging from 1 to 40 atms.

16. Process for the transalkylation of a polyalkylated benzene according to claim 11, wherein the reagents are fed to the reaction at a feeding rate WHSV ranging from 0.5 to 30 $h^{-1}$.

* * * * *

UNITED STATES PATENT AND TRADEMARK OFFICE
CERTIFICATE OF CORRECTION

PATENT NO. : 5,650,547
DATED : July 22, 1997
INVENTOR(S) : Fabrizio Cavani, Gianni Girotti, Virginio Arrigoni and Giuseppe Terzoni It is certified that error appears in the above-indentified patent and that said Letters Patent is hereby corrected as shown below:

On the title page: Item

[73] Assignee: Ministero Dell 'Universita' E Della Ricerca Scientifica E Tecnologica, Italy Signed and Sealed this Eleventh Day of November, 1997

Attest:

BRUCE LEHMAN

Attesting Officer

Commissioner of Patents and Trademarks